United States Patent [19]
Reddy

[11] Patent Number: 4,621,058
[45] Date of Patent: Nov. 4, 1986

[54] METHOD OF PREPARING CHEESE STARTER MEDIA

[75] Inventor: Malireddy S. Reddy, Aurora, Colo.

[73] Assignee: Mid-America Dairymen, Inc., Springfield, Mo.

[21] Appl. No.: 597,051

[22] Filed: Apr. 9, 1984

Related U.S. Application Data

[63] Continuation-in-part of Ser. No. 483,508, Apr. 11, 1983, abandoned.

[51] Int. Cl.[4] .................... C12N 1/20; A23C 19/00; A23C 21/02
[52] U.S. Cl. .................... 435/253; 426/36; 426/41; 426/43
[58] Field of Search ............. 435/253; 426/34, 36, 426/41, 42, 43, 583

[56] References Cited

U.S. PATENT DOCUMENTS

| | | | |
|---|---|---|---|
| 3,041,248 | 6/1962 | Hargrove | 426/39 X |
| 3,192,124 | 6/1965 | Kheshgi | 426/43 X |
| 3,998,700 | 12/1976 | Reinbold et al. | 426/43 X |
| 4,020,185 | 4/1977 | Anderson et al. | 426/36 |
| 4,115,199 | 9/1978 | Porubean et al. | 426/43 |
| 4,289,788 | 9/1981 | Cajigas | 426/41 X |
| 4,289,789 | 9/1981 | Cajigas | 426/41 X |
| 4,402,986 | 9/1983 | Sinkoff et al. | 426/36 X |
| 4,444,800 | 4/1984 | Bixby et al. | 426/582 |

OTHER PUBLICATIONS

CRC Handbook of Food Additives, 2nd, ed., vol. I, CRC Press, Cleveland, Ohio, 1972, (p. 630).
The Condensed Chemical Dictionary 10th ed., Van Nostrand Reinhold Co., N.Y., 1981, p. 877.
Webb, et al., Byproducts From Milk, 2nd ed., The Avi Publ. Co., Inc., Westport, Conn., 1970, pp. 26-27.

*Primary Examiner*—David M. Naff
*Attorney, Agent, or Firm*—Schmidt, Johnson, Hovey & Williams

[57] ABSTRACT

Low cost, readily dispersible, phage-resistant cheese starter media are described which include milk-derived nutrients (e.g., nonfat milk and whey) along with a minor proportion of preferably free or unbound lecithin. The media also may advantageously include sodium tetraphosphate which assists in the dispersion of whey solids. The media of the invention can be used at significantly lower levels as compared with nonfat dry milk solids (e.g. 7 percent versus 12 percent), while nevertheless obtaining essentially equivalent results in terms of culture growth and final culture properties. A method of producing the media is also disclosed, involving liquid preblending of phosphates and lecithin, followed by addition thereof to milk-derived nutrients and reaction of the phosphates to tie up free calcium ion. Preferably, reaction is carried out for about 1 to 12 hours while agitating. The final step involves drying of the mixture to yield a substantially homogeneous, reconstitutable powder. In other cases the phosphate-lecithin preblend can be dried for later addition to milk-derived nutrients to produce a final starter medium.

10 Claims, No Drawings

METHOD OF PREPARING CHEESE STARTER MEDIA

This is a continuation-in-part of application Ser. No. 06/483,505, filed Apr. 11, 1983, now abandoned, and entitled "Cheese Starter Media."

BACKGROUND OF THE INVENTION

1. Field of the Invention

The present invention is broadly concerned with novel, low cost cheese starter media which can be used by cheese makers in the growth of bulk starter cultures, along with a unique method of producing the media. More particularly, it is concerned with such media which in preferred forms include a minor amount of free or unbound lecithin, and/or minor quantities of sodium tetraphosphate for purposes of imparting a stable, homogeneous disperson of the starter media ingredients; in its method aspects, the invention involves preparation of a liquid preblend including phosphate anti-bacteriophage agent(s) and, preferably, lecithin, and mixing of the preblend with milk-derived nutrients (e.g., whey and nonfat milk), followed by drying to yield a smooth, consistent, substantially uniform and homogeneous reconstitutable powder.

2. Description of the Prior Art

In the manufacture of natural cheese, milk in a cheese vat is inoculated with a minor amount (e.g. 2–4 percent) of a bulk starter providing the necessary culture of acid-forming microorganisms used for the particular cheese being manufactured. For example, in the case of Italian cheeses such as mozzarella, it is the usual practice to employ *Streptococcus thermophilus* together with one or more lactobacilli such as *Lactobacillus bulgaris*. In the art, the streptococci are generally referred to by the short name of "coccus", while the lactobacilli are referred to as "rod" bacteria because of their appearance under microscopic examination.

The quantity and activity of cheese-making microorganisms can be critical to the overall outcome of the process and final cheese quality. Again referring to Italian cheese, it has been found that, in order to make acceptable cheese, the ratio of coccus to rod microorganisms in the starters should be from about 1:1 to 5:1, the most preferable level being about 2:1 to 3:1. If these ratio considerations are not met, the final Italian cheese product may be deficient in flavor or physical properties such as elasticity and "stringiness."

It is the universal practice among cheese makers to grow their bulk starters using relatively minor amounts of seed culture. In such techniques, the seed culture is inoculated into a starter medium and allowed to incubate therein so that the culture cells will multiply to produce the desired bulk starter for use in cheese making. Here again, the types of starter media and the techniques used during the incubation process can have a relatively critical outcome on the quality of the final bulk starter, and hence on the cheese ultimately produced. A dilute dispersion of nonfat milk (e.g., 12 percent slids level) in water has long been considered the starter medium of choice. However, use of nonfat milk in this context is a relatively expensive proposition, and therefore cheese makers have in the past sought to use media of a less expensive nature which either eliminate nonfat milk entirely, or sharply limit its use by provision of substitute materials.

For example, U.S. Pat. No. 3,852,158 describes a starter media which includes milk-derived materials, a nitrogen source, and citrate anion. In preferred forms, the starter media described in this patent contain a major amount of sweet whey and a minor amount of nonfat dry milk solids.

U.S. Pat. No. 3,998,700 describes starter media which include both acid and sweet whey solids together with nonfat dry milk solids. Finally, U.S. Pat. No. 2,805,950 describes the use of whey for culturing bacterial microorganisms used in making a swiss cheese.

While a number of alternative starter media have thus been proposed in an attempt to provide an acceptable substitute for expensive nonfat milk, none of these media have given results completely equivalent to that of the nonfat milk. In many cases, the alternative media do not provide the ideal environment for bacterial growth, or in the case of Italian cheese making, the final coccus to rod ratio obtained may be improper. Moreover, in those media which incorporate relatively large quantities of whey, a problem arises by virtue of the phenomenon known as "whey out." Specifically, large amounts of whey in a starter medium can precipitate to the bottom of the starter tank and create severe handling problems. In fact, these problems can become so severe that some cheese makers simply refuse to use starter media containing substantial amounts of whey, even if growth characteristics of such media are satisfactory.

U.S. Pat. No. 3,041,248 to Hargrove describes the use of various phosphates for the control of bacteriophage, which are active against lactic acid bacteria. Indeed, the many starter media presently available include various phosphates for the purpose of combatting bacteriophage. In this connection, it is known that the phosphates react with or tie up the readily available calcium ion present in the media, and this in turn prevents the bacteriophage from adsorbing onto the specific starter bacterium. In conventional practice, the phosphates are simply added directly to the remaining dry ingredients of a starter medium, followed by appropriate blending and bagging. This conventional dry blending procedure presents a number of practical problems in the use of starter medium, however, particularly with respect to the phosphate content thereof.

Specifically, the phosphates tend to be of irregular, grainy appearance and size in a dry condition, and therefore tend to settle out or stratify in the dry blended media. When the media are reconstituted in water, problems are presented not only from the standpoint of solubility (the conventional media are sometimes difficult to disperse in water), but more important the phosphates present may not completely react with free calcium ion. In order to ensure the most effective use of the phosphate anti-bacteriophage agents, it is desirable that the dry medium be smooth, uniform and substantially homogeneous; and this is particularly the case when it is borne in mind that the media may be used with radically different equipment and cheese-making practices from manufacturer to manufacturer. Non-uniformity inevitably means that in certain portions of the media the phosphate concentration is too low, while in other portions it is too high; and both of these conditions should be avoided.

In addition, when a typical dry blended powder medium is reconstituted in water, it is desirable to allow sufficient time for the phosphate to react with available calcium. Under normal cheese plant conditions, however, this reaction time should be minimized, and in some instances time constraints have forced cheese makers to employ a starter medium which has been insufficiently reacted; the result of this is that the problem of bacteriophage may not have been completely eliminated, and this in turn can have severe consequences in terms of cheese production.

In short, the irregular, non-uniform nature of many dry blended starter media compositions lead to a number of rather serious problems, most particularly with respect to the proper utilization of phosphate anti-bacteriophage agents present therein.

Accordingly, there is a heretofore unsatisfied need in the art for less expensive, alternative starter media, and a method of production thereof, which can be used in lieu of nonfat milk per se while giving essentially equivalent results in terms of culture growth and qualities, and which avoids practical difficulties such as "whey out" and problems stemming from non-uniformity.

SUMMARY OF THE INVENTION

The problems outlined above are in large measure solved by the present invention which provides greatly improved starter media for cheese making microorganisms. A principal advantage of the invention is the fact that dried media can be readily produced which are virtually homogeneous and give the appearance of a fine, talcum-like powder. The uniformity of the media of the invention facilitates reconstitution and dispersal thereof in water or other aqueous media and substantially prevents differential phosphate concentrations.

In terms of production methods, dried, reconstitutable bacteriophage-resistant starter media for cheese-making microorganisms are produced by first providing a quantity of milk-derived nutrient such as whey, nonfat dry milk solids, or a combination of the foregoing. In the next step, a liquid preblend is prepared, separately from the first quantity of milk-derived nutrients, with the preblend having a phosphate anti-bacteriophage agent dispersed therein. Advantageously, this preblend also includes a quantity of lecithin along with appropriate minerals. The liquid preblend is then added to the milk-derived nutrients to form a liquid mixture, and this mixture is then allowed to react for a period of, typically, 1–12 hours in order to permit the phosphates to react with available calcium ion in the mixture. In the final manufacturing step, the reacted mixture is dried, usually using conventional spray drying techniques.

In preferred manufacturing procedures, the pH of the milk-derived nutrients is adjusted to a level of from about 6.0 to 7.5 prior to the addition of the liquid preblend. Further, the milk-derived nutrients may be partially concentrated to a solids level of from about 25 to 50 percent, and the temperature thereof is advantageously adjusted to from about 35 to 60 degrees Fahrenheit, in order to facilitate dispersal of the preblend therein.

The preblend is normally prepared by heating a qauntity of water to a temperature of from about 85 to 130 degrees Fahrenheit, followed by addition of the phosphate agent(s) such as mono and disodium phosphate and sodium tetraphosphate to the heated water, with agitation to achieve a substantially uniform dispersion. In preferred procedures, an amount of free or unbound lecithin is also added to the preblend mixture.

The final dried starter media in accordance with the invention are very uniform and homogeneous, and exhibit extremely desirable physical characteristics which greatly facilitate their use. As noted, such media in dried form broadly comprise a milk-derived nutrient and a minor amount of unbound lecithin. The milk-derived nutrients used in the preferred starter media advantageously comprise relatively modest amounts of nonfat milk, and major proportions of whey. Starter media in accordance with the invention which include substantial whey fractions are greatly improved by the addition of a minor amount of sodium tetraphosphate therein, which as noted is added with the other phosphates in the liquid preblend. This additive has been found to greatly assist in the aqueous dispersion of the whey, and largely eliminates the problem of "whey out."

The addition of free or unbound lecithin to the starter media hereof has been found to give enhanced results in terms of culture growth and final bulk starter properties; indeed, the preferred media of the invention give essentially equivalent results, as compared with use of nonfat dry milk solids in aqueous dispersion. In fact, such equivalent results obtain through the use of significantly smaller quantities of the present media, as compared with NFDM. Specifically, a 7 percent solids dispersion of the preferred media of the invention gives virtually identical results, as compared with a 12 percent solids dispersion of NFDM.

As used herein, the term "free" or "unbound" in conjunction with lecithin refers to lecithin in relatively purified form which is substantially free of chemical and/or physical bonding to other materials. Such free or unbound lecithin is to be contrasted with, for example, lecithin which may be found in products such as fresh milk or buttermilk. In such context, the relatively minor lecithin content is believed to exist as a lipoprotein where the lecithin is in a complex with the protein. Such association with other constituents may have the effect of altering the properties of the lecithin in the context of starter media; accordingly, use of the free or unbound lecithin as herein defined is preferred.

The media of the invention also advantageously include minerals such as manganese chloride and ferrous ammonium sulphate, and a corn steep solids/whey solids stimulant.

Although in preferred forms a complete dried starter medium is provided in accordance with the invention, in other instances a dried preblend can be produced for addition to sweet whey or other milk-derived nutrients to produce a complete starter medium. Such a preblend would comprise a dried, substantially uniform powder having therein respective quantities of a phosphate anti-bacteriophage agent, lecithin and optionally NFDM, corn steep stimulant and minerals (e.g., ferrous ammonium sulfate and/or manganese chloride). The lecithin is preferably free or unbound as defined, and is advantageously present at a level of from about 0.1 to 0.8 percent by weight (most preferably, 0.5%).

DESCRIPTION OF THE PREFERRED EMBODIMENTS

In practice, one of the most preferred starter media of the invention is in the form of a dried composition which can be added to an aqueous system to give a liquid starter medium. This composition includes the following components:

TABLE I

| Ingredient | Initial Quantity[1] | Parts by Wt. of Dried Composition (Dry Basis) |
|---|---|---|
| Stimulant | 700 lbs. | 4.120 |
| Nonfat dry milk solids | 900 lbs. | 5.290 |
| Sodium tetra phosphate | 800 lbs. | 4.700 |
| Disodium phosphate | 550 lbs. | 3.230 |
| Monosodium phosphate | 800 lbs. | 4.700 |
| Manganese chloride | 400 gr. | 0.005 |
| Ferrous ammonium sulphate | 400 gr. | 0.005 |
| Lecithin[2] | 5 gallons | 0.290 |
| Sweet liquid whey[3] | 280,000 lbs. | 77.660 |

[1]Total weight or quantity, including free water, of starting ingredients
[2]Lecithin in liquid form, 50% by wt. solids; or could be in the form of a dried powder
[3]May alternatively be derived by mixing 13,198 lbs. of dried whey with 266,802 lbs. of water The preferred dried powder media composition is made as follows. In the first step, 700 pounds of the stimulant (a dried mixture of corn steep solids and sweet whey solids described in detail below), along with 900 pounds of the nonfat dry milk solids are mixed with the 280,000 pounds of liquid sweet whey (either raw or pasteurized, normally pasteurized). After sufficient mixing to disperse the stimulant and milk solids, the mixture is neutralized by the addition of sodium hydroxide (50%) to a pH of 6.0-7.5 (preferably 7.0). The pH adjusted mixture is then thermally evaporated under vacuum conditions to a 25-50 percent solids level (preferably 41%), whereupon the mixture is cooled to 35-60 degree Fahrenheit (preferably 50° F.) and transferred to a final mixing tank.

A phosphate/minerals/lecithin premix is prepared separately from the mixture of stimulant, dried milk and whey. This premix is made by adding 375 gallons of water at 85-130 degrees Fahrenheit (preferably 96° F.) to a 1,000 gallon mixing tank. Next, 800 pounds of sodium tetra phosphate is added, followed by 800 pounds of monosodium phosphate and 550 pounds of disodium phosphate, all with constant agitation. The next step involves dissolving the 400 grams of ferrous ammonium sulfate and 400 grams of manganese chloride in a small amount of water, whereupon these minerals are added to the agitated mixture of water and phosphates. The 5 gallons of lecithin is then added to the premix tank, again with sufficient agitation to ensure homogeneity. Other phosphate anti-bacteriophage agents can of course be employed in place of the preferred phosphates listed above, e.g., ammonium phosphates. Moreover, while dry granular phosphates can be added and dissolved, in other instances these can be made in plant by mixing the starting ingredients, e.g., appropriate quantities of phosphoric acid and ammonia can be reacted to form the desired ammonium phosphates, and the products used directly without an intermediate drying step.

This premix is then added to the mixture of whey, stimulant and dried milk solids, whereupon the overall mixture is agitated for 1-12 hours, and preferably overnight, in order to assure that the phosphates react with available calcium ion in the mixture. The reacted mixture is then spray dried to about 3-6 percent moisture (preferably 4%) to yield a substantially uniform and homogeneous, flowable, dried, powder-like material. Of course, if the medium is made in the plant where it is to be used, it may be advantageous not to dry the medium but rather to use the same directly with appropriate dilution to achieve the desired solids content for the final liquid medium, i.e., from about 5 to 15 percent, and more preferably from about 7-11 percent.

In other cases, however, the phosphate/minerals/lecithin premix can be formulated alone and dried, whereupon it can later be added to whey or other milk-derived nutrients to yield a final medium. This procedure gives some of the advantages of the preferred techniques described above, and avoids the expense of drying, storing and shipping of large quantities of whey and the other components of the complete medium.

The stimulant referred to above is made by taking 280,000 pounds of separated raw whey from the cheese-making vat (such amount of whey being a separate quantity from that used in the starter media per se listed in Table I), and adjusting the pH thereof to a level of about 8.0 with sodium hydroxide. The pH-adjusted whey is then evaporated to a 34 percent solids level, and cooled to 50 degrees Fahrenheit. The evaporated whey is then pumped into a tank containing 42,880 pounds of commercially purchased corn steep liquor having a pH of 4.15. Such liquor is obtained from The Staley Corporation of Decatur, Ill., and has a 50 percent solids level. This creates a mixture containing about 60 percent by weight corn steep solids and 40 percent by weight whey solids. The 60 percent-40 percent mixture is then agitated overnight, filtered and spray dried to about 4 percent moisture. The resultant dried product is stored in 50 pound bags for subsequent use in the starter media. An alternate stimulant can be produced by replacing the corn steep liquor with liquid yeast extract or any other suitable liquid stimulant.

The above described dried media composition can be used to obtain starter media for various types of microorganisms used in cheese making. For example, in order to obtain a starter media specifically designed for culturing microorganisms used in making Italian cheeses such as mozzarella (referred to as "coccus" and "rod" microorganisms), the following procedure is followed. First, 3,950 pounds (476 gallons) of fresh water is pumped into the starter tank, and the water is heated to a level of 100-110 degrees Fahrenheit. Three hundred pounds of the dried starter medium of Table I above is next added to the water, with the aid of a powder horn. The pH of this mixture will be about 6.6±0.1. The mixture is then heated to 190 degrees Fahrenheit and held for one hour at this temperature, whereupon the mixture is cooled to a temperature of 100-112 degrees Fahrenheit. At this point, the mixture is ready for inoculation with the desired coccus and rod cultures.

In another example, a dried composition very similar to that described above can be employed to prepare a culture medium for lactic cultures to be used in making American-type cheeses. From a compositional standpoint, the only difference involves the addition of a total of 2200 grams of ferrous sulfate. In this technique, 3,950 pounds (476 gallons) of fresh water is pumped into the starter tank, and is heated to a temperature of 100-130 degrees Fahrenheit. Three hundred pounds of the modified dried starter medium is next added to the heated water with the aid of a powder horn, giving a resultant pH of the mixture of approximately 6.6±0.1. The mixture is then heated to 190 degrees Fahrenheit, and held at this temperature for 1 hour, whereupon the medium is cooled to 74–80 degrees Fahrenheit. Here again, at this point in the procedure, the medium is ready for inoculation with the appropriate lactic cultures.

While in many instances the preparation of a complete, dried composition of the type described above is advantageous for reasons for ease of handling or the like, the invention is not so limited. That is to say, in appropriate circumstances a cheese manufacturer may wish to use whey derived directly from the cheese making operation, as opposed to having whey in the dried media composition. In such a case, one option would be to prepare a supplement mixture which can be added to liquid whey to produce a final liquid starter media. The stimulant, phosphates, minerals, nonfat dry milk and lecithin are premixed either by dry or wet blending, and are added to liquid whey. The pH of the mixture is then adjusted to a level of 6.6–6.7 through addition of, e.g., sodium hydroxide or ammonia, and the mixture is heated to 190 degrees Fahrenheit and held at that temperature for one hour. The mixture is then cooled to 100–112 degrees Fahrenheit, whereupon it is ready for inoculation with a desired culture.

EXAMPLE 1

In this test a comparison was made between the two starter media, namely nonfat dry milk solids, and the most preferred lecithin-containing composition of the invention, in terms of final coccus/rod ratios, bacterial counts and the activities achieved using the respective media.

The nonfat dry milk was reconstituted in water at 12.0% solids in water, whereas the medium hereof (Table I) was reconstituted in water at a level of only 7 percent solids. Both media were heat treated by heating to 190 degrees Fahrenheit and holding at this temperature for one hour. The media were then cooled to 102 degrees Fahrenheit and inoculated with identical quantities (1%) of coccus and rod cultures (*Streptococcus thermophilus* and *Lactobacilus bulgaris*). The cultures were then incubated in the respective media at 102 degrees Fahrenheit until the titratable acidity exceeded 1.0; for the NFDM system this took about 5.5 hours, and for the medium of the invention about 7 hours. At this point the cultures were cooled to 40 degrees Fahrenheit. The two cultures were then tested for titratable acidity, coccus/rod ratio, pH and activity, all using conventional techniques. The results of this test were:

TABLE II

| Media | Final pH | Final Titratable Activity | Coccus/ Rod Ratio | Total Bacterial Count | Activity |
|---|---|---|---|---|---|
| NFDM (12%) | 4.20 | 1.02 | 4:1 | 140 × 10⁷ | 0.70 |
| Invention (7%) | 4.35 | 1.02 | 4:1 | 130 × 10⁷ | 0.72 |

As noted in Table II, the results using the costly NFDM are very similar to those obtained with the medium of the invention. This is very surprising in that a significantly greater quantity of NFDM was employed (12%) versus the invention (7%). At present day typical retail costs, the cost of using the medium of the invention to achieve equivalent results is on the order of only 50 percent of that of using NFDM as a starter medium.

In another similar test, equal percentage solids amounts of NFDM and the medium of the invention were tested (7% solids used in both cases). These tests were conducted in the same manner as heretofore described except that the 7 percent solids NFDM media was incubated after inoculation until the pH reached about 4.25; this is the pH level where NFDM systems normally give a titratable acidity of greater than 1.0. That is to say, if a 7% solids NFDM system is allowed to incubate to a 1.0% or greater titratable acidity, the pH would be abnormally low (e.g., around 3.7), and the bacteria would be injured or the coccus/rod ratio would be totally unacceptable.

Accordingly, the incubation of the 7 percent NFDM system was terminated at the normal pH achieved for full strength NFDM media, which took about 5 hours. On the other hand, the medium of the invention was incubated for a period of about 7 hours until the titratable acidity exceeded 1.0. The final results were:

TABLE III

| Media | Final pH | Final Titratable Activity | Coccus/ Rod Ratio | Total Bacterial Count | Activity |
|---|---|---|---|---|---|
| NFDM (7%) | 4.25 | 0.79 | 3:1 | 68 × 10⁷ | 0.58 |
| Invention (7%) | 4.45 | 1.01 | 4:1 | 120 × 10⁷ | 0.71 |

Thus, the low solids NFDM system proved deficient in titratable acidity, bacterial count, and activity, as compared with the invention. Moreover, on a cost basis the medium of the invention is far superior, even at equal solids levels.

EXAMPLE 2

In this example, a comparative test was made between a medium in accordance with the invention (Table I) prepared using the preblending and drying procedure of the invention, versus a compositionally identical medium made simply by dry blending all of the ingredients (the lecithin used in this case was also a dried powder). The separate media were then reconstituted in 60 degrees Fahrenheit water, with agitation as necessary to a 7 percent solids level, and cooked at 190 degrees Fahrenheit for one hour. The media were then cooled to 104 degrees Fahrenheit and inoculated with 0.1 ml. of milk grown coccus and rod culture.

The inoculated media were then incubated until the pH thereof dropped to 4.8 (about 5½ hours), whereupon the pH was raised to 6.2 by the addition of 50 percent sodium hydroxide. The incubations were then allowed to continue until the titratable acidity in both cases was 1.10. With the liquid preblend, spray dried medium of the invention, this took a total of about 10½ hours, whereas with the dry blended medium a total incubation time of 11¼ hours was required.

At this point the media were cooled to 55 degrees Fahrenheit and tested as set forth in certain entries of the following Table:

TABLE IV

COMPARISONS OF LIQUID PREBLENDING AND DRYING vs. SIMPLE DRY BLENDING ON THE PHYSICAL AND CULTURE GROWTH-SUPPORTING PROPERTIES OF STARTER MEDIA

| Comparison Number | Characteristics | Liquid Preblend Spray Dried Medium | Dry Blended Medium |
|---|---|---|---|
| 1. | Physical Appearance | Smooth and uniform-similar to talcum powder | Gritty and Irregular sizes of the various ingredients evident |
| 2. | Stratification of the media | None | Stratified-Phosphates Tend to settle down in the powder |
| 3. | Solubility | Instantly soluble even in the 60° F. water | 5 minutes agitation required to solubilize in the 60° F. water |
| 4. | Initial pH of the powdered medium when reconstituted | 6.65 | 6.30 |
| 5. | Precipitation upon reconstitution and heating | None | Considervisible precipitates settled to bottom |
| 6. | Time to grow coccus and rod culture using the 1 step neutralization to arrive at final 1.10 titratable acidity | 10½ hrs. | 11¼ hrs. |
| 7. | Coccus/rod ratio after growth | 3:1 | 1:1 |
| 8. | Total bacterial count per gram after culturing | $230 \times 10^7$ | $200 \times 10^7$ |
| 9. | Activity measured in terms of titratable acidity | 0.65 | 0.63 |
| 10. | Smoothness of liquid medium after growth of culture | Smooth | Grainy-an appearance of buttermilk |

The foregoing Table demonstrates the many advantages obtained through use of the liquid preblend-drying procedure for producing starter media. The smooth, uniform, essesntially homogeneous nature of the media of the invention not only facilitates quick, easy handling, but also gives measurably enhanced results in terms of desirable coccus/rod ratios, bacterial counts and activities.

EXAMPLE 3

This example sets forth another preferred media composition in accordance with the invention, which has been formulated to reduce the incubation time needed to reach a final titratable acidity level of about 1.10 from an average of 10½ hours to about 7½-8½ hours.

TABLE V

| Ingredient | Quantity Used |
|---|---|
| [1]Yeast extract | 850 lbs. |
| Nonfat dry milk powder | 1,000 lbs. |
| Disodium phosphate | 1,479 lbs. |
| Monosodium phosphate | 221 lbs. |
| Ferrous ammonium sulfate | 17 lbs. |
| Manganese chloride | 450 grams |
| [2]Lecithin | 2½ gallons |
| Sweet liquid whey | Balance to yield 17,000 lbs. batch of dried medium |

[1]Employed as a stimulant
[2]50% solids liquid lecithin

The medium of Table IV is made as outlined above in Example 1. In the first step the liquid whey, NFDM powder and yeast extract are mixed and ammonium hydroxide or anhydrous ammonia is added to adjust the pH to 7.0, followed by drying to about 40 percent solids and cooling to 50 degrees Fahrenheit. A liquid preblend of lecithin, the phosphates and the minerals is then made by dispersing these ingredients in 96 degrees Fahrenheit water as outlined in Example 1. The preblend is then added to the cooled nutrients, and the mixture is allowed to react overnight, and the pH is then adjusted as necessary using $NH_4OH$ or anhydrous ammonia. Finally, the mixture is spray dried to about 4% moisture.

EXAMPLE 4

A highly preferred lactic culture medium for growing cheddar cheese starter microorganisms is set forth below:

TABLE VI

| Ingredient | Quantity Used |
|---|---|
| [1]Corn steep solids | 1,360 lbs. |
| [1]Yeast extract | 425 lbs. |
| Nonfat dry milk powder | 1,000 lbs. |
| Sodium tetraphosphate | 840 lbs. |
| Disodium phosphate | 435 lbs. |
| Monosodium phosphate | 1,275 lbs. |
| Manganese chloride | 250 grams |
| Ferrous ammonium sulfate | 10 lbs. |
| [2]Lecithin | 2½ gallons |
| Sweet liquid whey | Balance to yield a 17,000 lb. batch of dried medium |

[1]Stimulants
[2]50% solids liquid lecithin

This medium is made as outlined above, wherein the corn steep solids, yeast extract, NFDM and whey are initially mixed, and a separate liquid preblend of the phosphates, minerals and lecithin in water is added thereto, followed by overnight reaction and drying.

The tests described in the foregoing examples were preformed as follows:

pH

Hydrogen ion concentration was determined using Beckman pH meter

Titratable Acidity 9 grams of the medium sample was titrated with 0.1N sodium hydroxide using phenophthalin as an indicator. A faint pink color indicated the end point.

Coccus and Rod Ratio

A one in ten dilution of culture in water was smeared on a clean glass slide, stained with methylene blue, and examined under a compound microscope. The ratio was determined on the basis of clump and individual counts.

Total Bacterial Count

The cultured samples were serially diluted in sterile phosphate buffered water according to the procedures outlined in the Standard Methods for the examination of dairy products and plated using tryptic soy agar fortified with 0.5 percent yeast extract. The plated samples were incubated at 37 degrees Centigrade for 4 days. The counting and expression of the test results were done according to the Standard Procedures.

Activity Test 2 grams of culture was inoculated into 100 ml. of sterile 10.0 reconstituted nonfat dry milk. The nonfat dry milk was pretested for the inhibitory compounds. The inoculated milk was incubated at 36 degrees Centigrade for 45 minutes. At the end of the incubation, the temperature was gradually increased to 46 degrees Centigrade within a span of 30 minutes and it was thereafter maintained at that temperature for a period of 1 hour. The samples were then chilled to prevent any further acid development. Ten grams of the sample was carefully weighed into a 25 ml. beaker. Ten drops of indicator (phenophthalein) was added and the entire contents were titrated against 0.1N sodium hydroxide until a faint pink color persisted for 15 seconds. The results were expressed as percent titratable acidity.

Although the above described specific culture media are preferred in terms of composition and method of preparation thereof, those skilled in the art will readily appreciate that the invention is not so limited. That is to say, in other forms of the inventions, various substitute and/or additional materials may be employed, as opposed to those specifically recited in Tables I, V and VI, and moreover the amounts of use can be varied for the respective components. To give but a few examples, the preferred corn steep solids/sweet whey solids stimulant can be employed in an amount from about 1-10 percent by weight, and more preferably from about 2-6 percent by weight (dry basis). Other possible stimulants useful in this context include yeast extract, hydrolyzed vegetable proteins, pancreatic enzyme digests, and protease-treated milk. Such stimulants serve as non-specific growth rate enhancers which increase the rate of acid production and growth. Stimulants of this type have been known in the past, particularly in the context of starter media which contain other materials besides strictly nonfat dry milk solids.

While the use of nonfat dry milk solids and whey is preferred in order to provide the requisite milk-derived nutrients for the overall media, other materials such as casein, the various caseinates, casein hydrolyzates, partially demineralized whey, and whey protein concentrates could also be used. In those instances where nonfat milk is employed, such should be present at a level of from about 1 to 10 percent by weight, and more preferably from about 4 to 6 percent by weight (dry basis). In like manner, when whey is employed, such should be present at a level of from about 50 to 90 percent by weight, and more preferably from about 70 to 80 percent by weight (dry basis).

As noted above, the use of sodium tetraphosphate in the media of the invention is preferred, particularly in those instances where a major proportion of whey is present. This serves to minimize the extent to so-called "whey-out" by aiding in the dispersion of the whey solids. Advantageously, the sodium tetraphosphate is present at a level of at least about 2 percent by weight, and more preferably from about 3 to 13 percent by weight (dry basis).

The disodium phosphate and monosodium phosphate additives are employed in the preferred composition in order to inhibit bacteriophage. The monosodium phosphate should be used at a level of from about 2 to 8 percent by weight (dry basis), whereas the disodium phosphate should be used at a level of about 3 to 13 percent by weight (dry basis). Moreover, the combination of sodium tetraphosphate with disodium phosphate and monosodium phosphate is particularly preferred inasmuch as this combination gives good whey dispersibility, bacteriophage protection, and a buffering capacity in the overall system.

While manganese chloride and ferrous ammonium sulfate have been employed in minor amounts as additive minerals, it will be readily seen that other minerals and levels of use can be employed. Particular minerals and optimum levels of use thereof are within the skill of the art.

The free or unbound lecithin forming a part of the preferred media of the invention should be present at a level of from about 0.05 to 25 percent by weight, and more preferably from about 0.20 to 1 percent by weight (dry basis). The utility of free or unbound lecithin in the media of the invention is not fully understood, but it is believed possible that the presence of lecithin (a phospholipid) improves the cellular integrity of the cheese-making microorganisms and thus promotes growth. In addition, lecithin is known to be an emulsifier, and could assist in the transport of nutrients into the cellular structure of the microorganisms. However, it will be appreciated that the foregoing represents hypothesis, and there is no wish to be bound to any sort of theory of operability in connection with use of lecithin.

During use of the media in accordance with the invention, it is desirable that the final liquid medium have a solid content of from about 5 to 15 percent by weight and more preferably from about 7-12 percent by weight, and most preferably from about 7-8 percent by weight. Obviously, use of the smallest amount of solids is preferred for economic reasons.

A variety of culture-growing techniques can be employed with use of the media of the invention. As noted above, the traditional technique of inoculating the medium with microorganisms at a starting pH in the range of, typically, 6.0-6.5, followed by incubation until the medium exhibits a pH in the range of 4.0-4.5, gives excellent results. In addition, certain other pH modification techniques described in recent years (see, e.g., U.S. Pat. No. 4,282,255) can be used to good effect in conjunction with the improved media of the invention.

I claim:

1. A method of making a dried, reconstitutable, bacteriophage-resistant starter medium for cheese-making microorganisms, said method comprising the step of:
   providing a quantity of liquid nutrient for said microorganisms including a major proportion of whey;
   preparing, separately from said quantity of nutrient, a liquid preblend having a phosphate anti-bacteriophage agent dispersed therein;
   adding said liquid preblend to said nutrient to form a liquid mixture, and allowing said agent to react with available calcium ion in said mixture, said reaction step comprising the step of agitating the liquid mixture for a period of from about 1 to 12 hours; and
   drying the reacted mixture to form a substantially uniform and homogeneous, flowable, dried starter medium.

2. The method of claim 1, said nutrient comprising sweet whey.

3. The method of claim 1, said nutrient comprising nonfat milk.

4. The method of claim 1, including the step of adjusting the pH of said quantity of nutrient to a level of from about 6.0 to 7.5.

5. The method of claim 1, including the step of evaporating said quantity of nutrient to a level of from about 25 to 50 percent solids.

6. The method of claim 5, including the step of cooling the evaporated nutrient to a level of from about 35° to 60° F.

7. The method of claim 1, said preblend preparation step comprising the steps of:

heating a quantity of water to a temperature of from about 85° to 130° F.; and adding said agent to the heated water, and agitating the resultant mixture to substantially uniformly disperse the agent therein.

8. The method of claim 7, said agent being selected from the group consisting of monosodium phosphate, disodium phosphate, sodium tetraphosphate and mixtures thereof.

9. The method of claim 1, including lecithin present at a level of from about 0.2 to 1.0% by weight in the final dried medium.

10. The method of claim 1, there being from about 50 to 90% by weight whey solids and from about 1 to 10% by weight nonfat milk solids in the final dried medium.

* * * * *